(12) United States Patent
Shi et al.

(10) Patent No.: US 6,483,933 B1
(45) Date of Patent: Nov. 19, 2002

(54) DIGITAL-TO-FILM RADIOGRAPHIC IMAGE CONVERSION INCLUDING A NETWORK

(75) Inventors: Shuanghe Shi, Southbrough, MA (US); James Martin Hill, Waukesha, WI (US); Kenneth Scott Kump, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/473,221

(22) Filed: Dec. 27, 1999

Related U.S. Application Data

(63) Continuation-in-part of application No. 09/224,240, filed on Dec. 30, 1998, now Pat. No. 6,201,890.

(51) Int. Cl.$^7$ .................................................. G06K 9/00
(52) U.S. Cl. .................................................... 382/132
(58) Field of Search ................................ 382/132, 190, 382/192, 194, 274, 312, 318, 319; 348/77, 332; 378/4, 5, 19, 22, 23, 62, 165; 290/582, 583, 585, 559.04, 559.05; 434/218, 267, 268, 269, 272, 274

(56) References Cited

U.S. PATENT DOCUMENTS

| | | | | |
|---|---|---|---|---|
| 5,046,118 A | * | 9/1991 | Ajewole et al. | 382/169 |
| 5,164,993 A | * | 11/1992 | Capozzi et al. | 382/132 |
| 5,172,419 A | * | 12/1992 | Manian | 382/132 |
| 5,447,153 A | * | 9/1995 | Weil et al. | 600/300 |
| 5,671,070 A | * | 9/1997 | Przybylowicz et al. | 358/487 |
| 6,067,342 A | * | 5/2000 | Gordon | 378/19 |

* cited by examiner

Primary Examiner—Andrew W. Johns
Assistant Examiner—Shervin Nakhjavan
(74) Attorney, Agent, or Firm—Foley & Lardner; Peter J. Vogel; Michael A. Della Penna

(57) ABSTRACT

A method for converting a digital image to an analog-simulative film-like digital image includes (a.) obtaining digital image input values for a number of pixels, each pixel having a digital image input value X, wherein the range of input values for all pixels defines the input dynamic range; (b.) for each pixel, determining an analog-simulative film-like output value $$Y = \sum_{i=1}^{M} A_i X^{Pi} + Bi$$

wherein $A_i$, pi, and $B_i$ are real numbers, and M is an integer value greater than or equal to 1; and (c.) communicating the analog-simulative film-like digital image or data associated therewith to a remote facility over a network.

20 Claims, 5 Drawing Sheets

DIGITAL-TO-FILM RADIOGRAPHIC IMAGE CONVERSION INCLUDING A NETWORK

CROSS-REFERENCE TO RELATED APPLICATIONS

This application is a continuation-in-part (CIP) of U.S. patent application Ser. No. 09/224,240, entitled "Digital-To-Film Radiographic Image Conversion" by Shuanghe Shi, James Martin Hill and Kenneth Scott Kump filed on Dec. 30, 1998 now U.S. Pat. No. 6,201,890.

BACKGROUND OF THE INVENTION

The present invention relates generally to the field of medical diagnostic systems, such as imaging systems. More particularly, the invention relates to a technique for digital-to-film radiographic image conversion.

The classic radiographic or "X-ray" image is obtained by situating the object to be imaged between an X-ray emitter and an X-ray detector made of photographic film. Emitted X-rays pass through the object to expose the film, with the degree of film exposure at the various points on the film largely being determined by the attenuation of the object along the path of the X-rays.

It is proposed to utilize solid-state digital X-ray detectors, e.g., an array of photodiodes, in place of film detectors. After the X-ray exposure is terminated, the charges generated on the various points of the detector are read and processed to generate a digital image of the object in electronic form, rather than an analog image on photographic film. Digital imaging is advantageous because the image can later be electronically transmitted to other locations, subjected to diagnostic algorithms to determine properties of the object, and so on.

However, digital images present problems when printed for analysis by radiologists. Because the characteristics of the digital detectors are significantly different from those of film, the images look quite different from analog film images, even when printed on transparent film. This is due to the differing exposure response curves of digital and film detectors. As an example, the digital image data generated by a detector may be linearly proportional to the received radiation (or nearly so), whereas film has a non-linear response to radiation. As a result, the contrast in digital images is not as great as that with radiographic film. To avoid error, radiologists analyzing digital images must keep these differences between analog and digital X-ray images prominently in mind when making such analyses. Therefore, there has been a need for a means of "translating" digital images into analog-simulative digital images which mimic the results of standard prior filmed images, and which may be printed on transparent film so that they resemble filmed radiographic images. This would allow the use of light boxes and other tools commonly in use for analysis of analog filmed images.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems above. In particular, there is a need for conversion or translation of digital images into images which approximate filmed images, communicating such images and image data over a network, and displaying such images.

SUMMARY OF THE INVENTION

One embodiment of the invention relates to a method for converting a digital image to an analog-simulative film-like digital image. The method includes (a.) obtaining digital image input values for a number of pixels, each pixel having a digital image input value X, wherein the range of input values for all pixels defines the input dynamic range; (b.) for each pixel, determining an analog-simulative film-like output value $$Y = \sum_{i=1}^{M} A_i X^{Pi} + B_i$$

wherein $A_i$, pi, and $B_i$ are real numbers, and M is an integer value greater than or equal to 1; and (c.) communicating the analog-simulative film-like digital image or data associated therewith to a remote facility over a network.

Another embodiment of the invention relates to a method for converting a digital image to an analog-simulative film-like digital image. The method includes (a.) obtaining digital image input values from a number of pixels, each pixel having an input value X, wherein the range of input values for all pixels defines the input dynamic range; (b.) for pixels having input values $X<X_1$ wherein $X_1$ is a value within the input dynamic range, determining for each pixel an analog-simulative film-like output value $Y=A_1 X^{p1}+B_1$ wherein $A_1$, $p_1$, and $B_1$ are real numbers and p1>1; (c.) for pixels having input values $X>X_2$ wherein $X_2$ is a value within the input dynamic range and $X_2 \geq X_1$, determining for each pixel an analog-simulative film-like output value $Y=A_3 X^{p3}+B_3$ wherein $A_3$, p3, and $B_3$ are real numbers and p3<1; (d.) generating an output image in accordance with the output values of the pixels; and (e.) communicating the output image or image data to a remote facility over a network.

Another embodiment of the invention relates to a method for converting a digital image to an analog-simulative film-like digital image. The method includes (a.) obtaining digital image input values from a number of pixels, each pixel having an input value X ranging between $X_{min}$ and $X_{max}$, the range between $X_{min}$ and $X_{max}$ defining the dynamic range of the input values; (b.) dividing the dynamic range into N intervals, N being an integer number of at least 1; (c.) for each interval, determining for each input value therein an analog-simulative film-like output value $$Y = \sum_{i=1}^{M} A_i X^{Pi} + B_i$$

wherein M is an integer value greater than or equal to 1, X is the input value, $A_i$, $p_i$, and $B_i$ are real numbers, and $p_i$ decreases with each interval after a first interval adjacent Xmin; and (d.) generating an output image in accordance with the output values of the pixels; and (e.) communicating the output image or image data to a remote facility over a network.

Other principle features and advantages of the present invention will become apparent to those skilled in the art upon review of the following drawings, the detailed description, and the appended claims.

DETAILED DESCRIPTION OF THE PREFERRED EMBODIMENT

As noted above, the preferred embodiment involves a method of converting digital images acquired from a radiographic detector into a digital form which simulates an analog film image. In this method, the value of each pixel within the digital image—which is received as an input from a corresponding photodiode (or other sensor) in the detector—is converted to an output analog-simulative value depending on its LSB (Least Significant Bit) value (grey level) within the dynamic range of the input radiographic image (i.e., the range of gradation of tones between lightest to darkest). The conversion, which is preferably provided by the processor receiving the pixel data from the detector, takes the following form:

$$Y = \sum_{i=1}^{M} A_i X^{p_i} + B_i$$

wherein

Y is the output analog-simulative value of the pixel,

X is the input digital pixel value (a gray level within the input dynamic range), M is an integer number greater than or equal to 1, and $A_i$, pi, and $B_i$ are appropriate real-number constants.

As will be discussed at greater length below, when performing the conversion, the dynamic range of the input digital image is preferably divided into N regions (N being an integer which is preferably greater than 1). A different conversion (i.e., different values for the constants $A_i$, pi, and $B_i$) is then preferably applied to each region.

Regarding the values of $A_i$, pi, and $B_i$, these are determined by simply choosing their values so that a desired response curve is obtained. If desired, regression techniques can be applied to experimental data to obtain $A_i$, pi, and $B_i$ values. It is noted that since the output may be viewed on different output devices, different values of $A_i$, pi, and $B_i$ may be appropriate for different versions of the invention using different types of output devices in order to obtain a more suitable analog-simulative output. As an example, one may expect that for two radiographic imaging systems which are equivalent save for their image output devices (e.g., the output devices have different output bit depths), $A_i$, pi, and $B_i$ will differ between the two systems.

Since the conversion is to mimic the nonlinear response curve of film, it can be expected that greater values of M will allow the conversion to more accurately match this response. However, greater values of M will also increase the computational burden of the conversion, and thus there is a tradeoff between enhanced output and processing times. In view of current processor speeds, the conversion has been found to yield entirely suitable results when M=1, that is, when the conversion is simplified to $$Y = AX^p + B$$

for each of the N regions. However, while the most preferred embodiment of the invention at present has M=1, as processor speeds increase in the future, it can be expected that it may become desirable to increase M and gain a more accurate film-simulative response.

Figure 1:
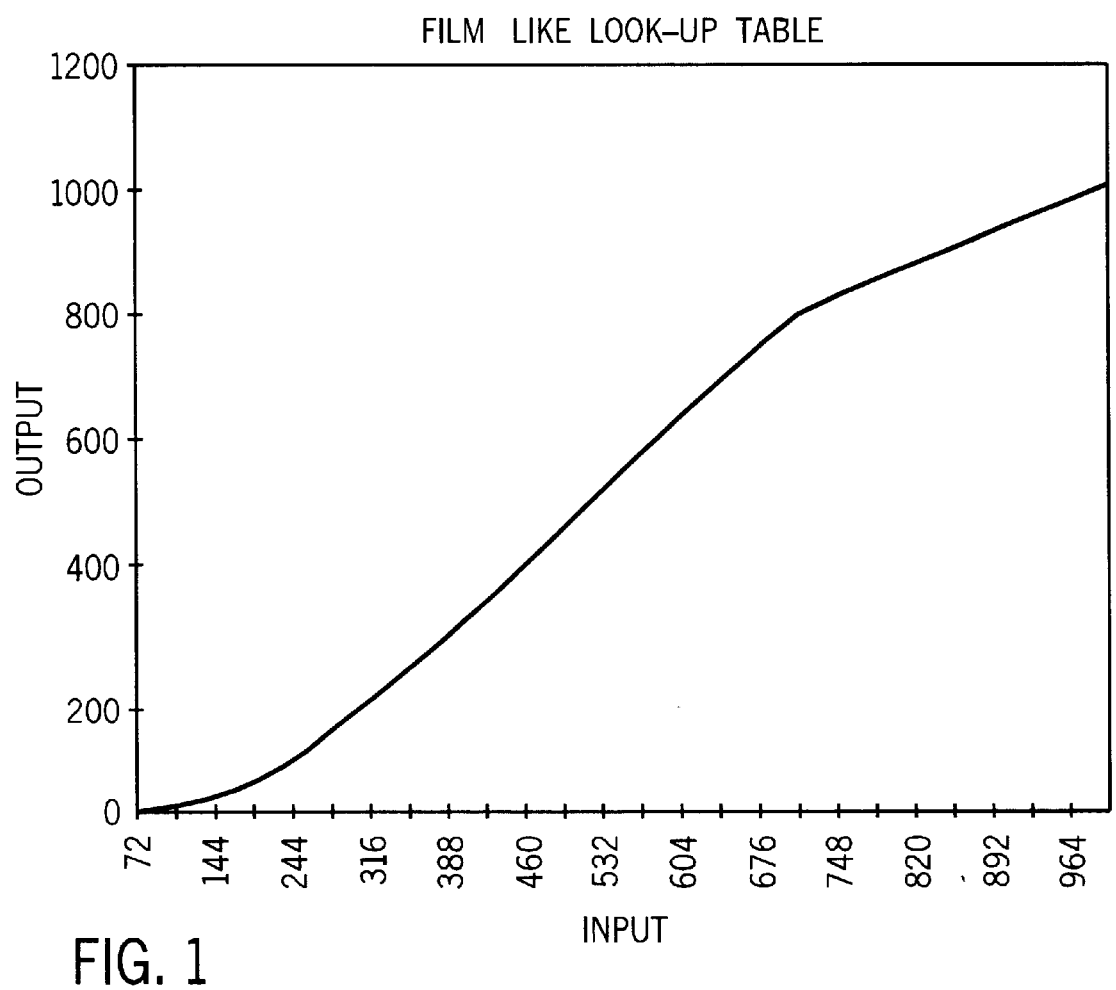
FIG. 1 is a graph of LSB (Least Significant Bit) values for pixels in an input digital image versus LSB values for an output analog-simulative film-like digital image in accordance with the invention.

Similarly, it has also been found suitable to use N=3, thereby defining three regions across the input dynamic range wherein the conversion is to be applied. The following equations describe the three regions (wherein reference is made to the corresponding FIG. 1 of the drawings):

Initially, a low light/radiation region (which corresponds to low light values such as those of bones in a chest image) is defined. It has been found that a generally good definition of the low light region is provided by $$X < X_1 \text{ where } X_1 = Q_1\% \ (X_{max} - X_{min}) \text{ and } Q_1 = 30$$

In other words, the low light region is defined as the lower 30% of the input dynamic range. The conversion is then applied by:

$$Y = A_1 X^{p_1} + B_1$$

and for image output devices having an output bit depth of 10 bits, $A_1$, p1, and $B_1$ have the following values:

$A_1$=0.000103

$B_1$=0.0 p1=2.5

In the low light region, the low light response curve of film is simulated by applying range compression (as effected by the small value of $A_1$, evidenced in FIG. 1 by the low responsiveness of the output values with respect to changes in the input values), but by also providing increasing responsiveness to increasing light levels (as effected by the value of p1 greater than 1). Apart from providing an accurate simulation of the low light response of film, the conversion also suppresses low-level quantum and electronic noise present in the input by attenuating the input at extremely low light levels.

A high light/radiation region (which corresponds to high light values such as those of the skin line in a chest image) may then be defined at the upper end of the input dynamic range. A generally good definition of the high light region is provided by $$X > X_2 \text{ where } X_2 = Q_2\% \ (X_{max} - X_{min}) \text{ and } Q_2 = 70$$

In other words, the high light region is defined as the upper 30% (or 100%–70%) of the input dynamic range. For image output devices having an output depth of 10 bits, the conversion is then applied by:

$$Y = A_3 X^{p_3} + B_3$$

where $A_3=41$ $B_3=-287$ $p3=0.5$

The high light response curve of film is simulated by applying range compression in the form of p3<1, thereby providing decreased output response to increasing input values.

The middle light/radiation region corresponds to medium light values such as those of organs and vessels in a chest image. For 10-bit output devices, the conversion in the middle light region, which is applied to input values $X_1<X<X_2$ (i.e., in the middle 40% of the dynamic range where the upper and lower regions are respectively set to the upper and lower 30% of the range), is expressed by $$Y=A_2X^{p2}+B_2$$

where $A_2=1.56$ $B_2=-308$ $p2=1$

By setting p2=1, the conversion for the middle light region is a linear one wherein $Y=A_2X+B_2$. Amplification/range expansion is provided by setting the slope $A_2>1$, thereby enhancing the contrast of the middle light region.

The values for the A, B, and p parameters, as well as for the $Q_1$ and $Q_2$ boundary values, may vary to some degree from those stated above. In the low light region, which will generally be defined with $5 \leq Q_1 \leq 40$ (i.e., the low light region will generally be defined at the lower 5%–40% of the input dynamic range), it will usually be desirable to apply range compression in the form of $A_1<1$ (and generally $A_1<<1$), and to also apply increasing responsiveness to increasing light levels by setting p1>1. The low light response region will thus provide the upwardly-sloping tail to the output/input curve shown in FIG. 1. In the middle light region, it will generally be desirable to provide approximately linear responsiveness by setting p2≈1, but to also provide range expansion by setting $A_2>1$. As for the high light region, it will generally be defined at the upper 60%–95% of the input dynamic range (i.e., $60 \leq Q_2 \leq 95$), and will provide a tail with decreasing slope such as that shown in FIG. 1. Conversely with the low light region, the parameters of the high light region are desirably set at $A_3>1$ (and generally $A_1>>1$), and p3<1.

It is notable that in the analog-simulative film-like output digital image, the optical density of the film-like image—the log base 10 ratio of the incident light intensity over the transmitted light density, a measure of the opacity of a transparent medium—may be set as desired at selected points on the dynamic range by choosing appropriate values for A, B, and p. This is most easily done by choice of an appropriate B value. Recommended optical density values at $X_1$ and $X_2$ to provide a high-quality film-like image are respectively 0.5 and 2.3, though variations from these values by as much as ±75% will still provide adequate results. It is also notable that the B values are preferably chosen such that the output curve is continuous between the N intervals.

As noted above, different output devices may require different A, p, and B values depending on their output bit depths. Stated more generally, when applying the conversions, the overall transfer function between the detector and the image display device (i.e., the monitor, printer, or other device used to view the analog-simulative film-like image) must be kept in mind; if an intermediate component applies some form of amplification or attenuation, the A, B, and p values may require modification to provide the desired conversion between the input detector image values and the output analog-simulative film-like image values.

Figure 2:
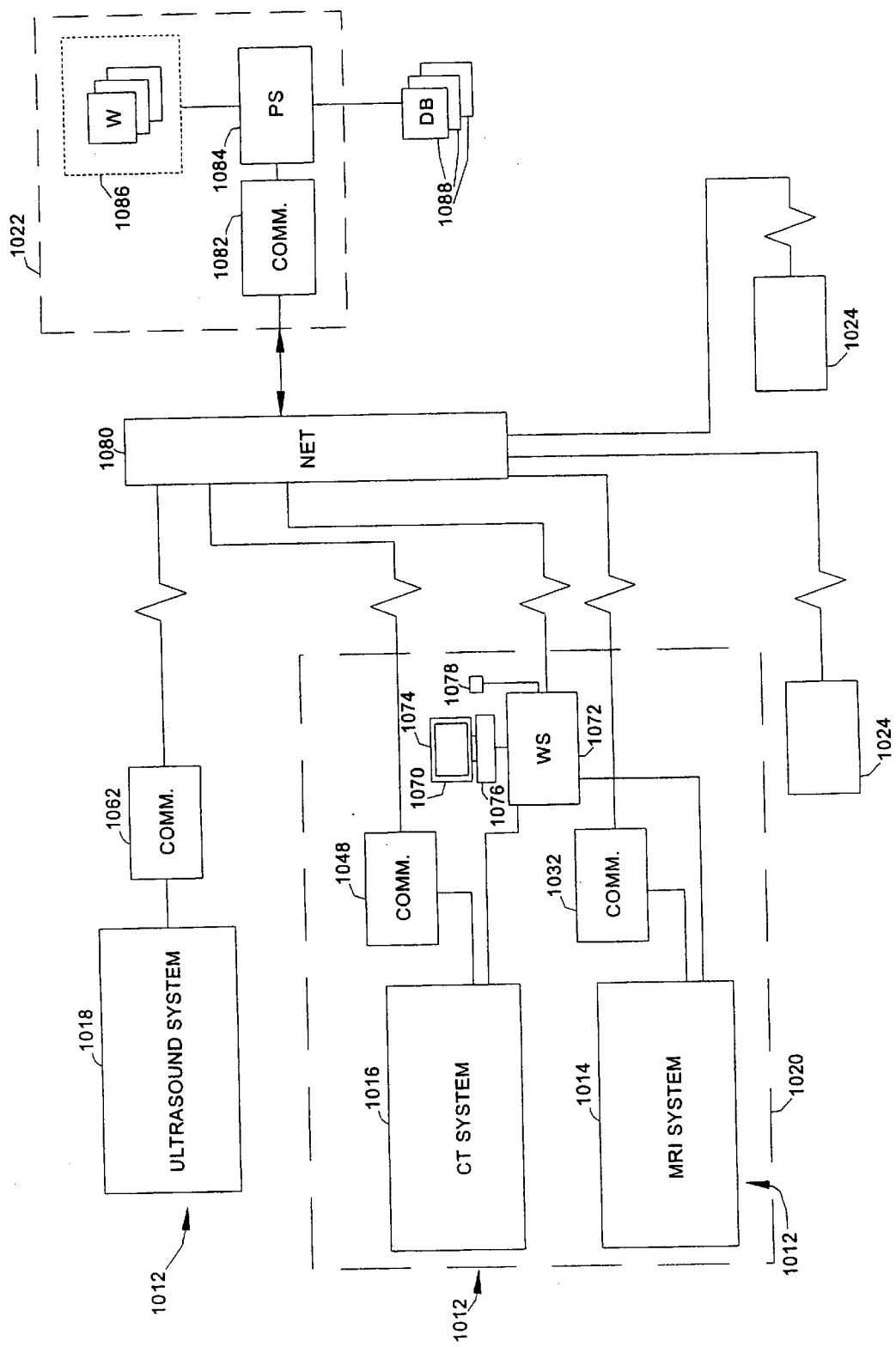
FIG. 2 is a diagrammatical representation of a series of medical diagnostic systems coupled to a service facility via a network connection for providing remote services and data interchange between the diagnostic systems and the service facility.

Referring now to FIG. 2, a service system 1010 is illustrated for providing remote service to a plurality of medical diagnostic systems 1012. In the embodiment illustrated in FIG. 2, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 2, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors.

Depending upon the modality of the systems, various subcomponents or subsystems will be included. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 2, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 2. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 3:
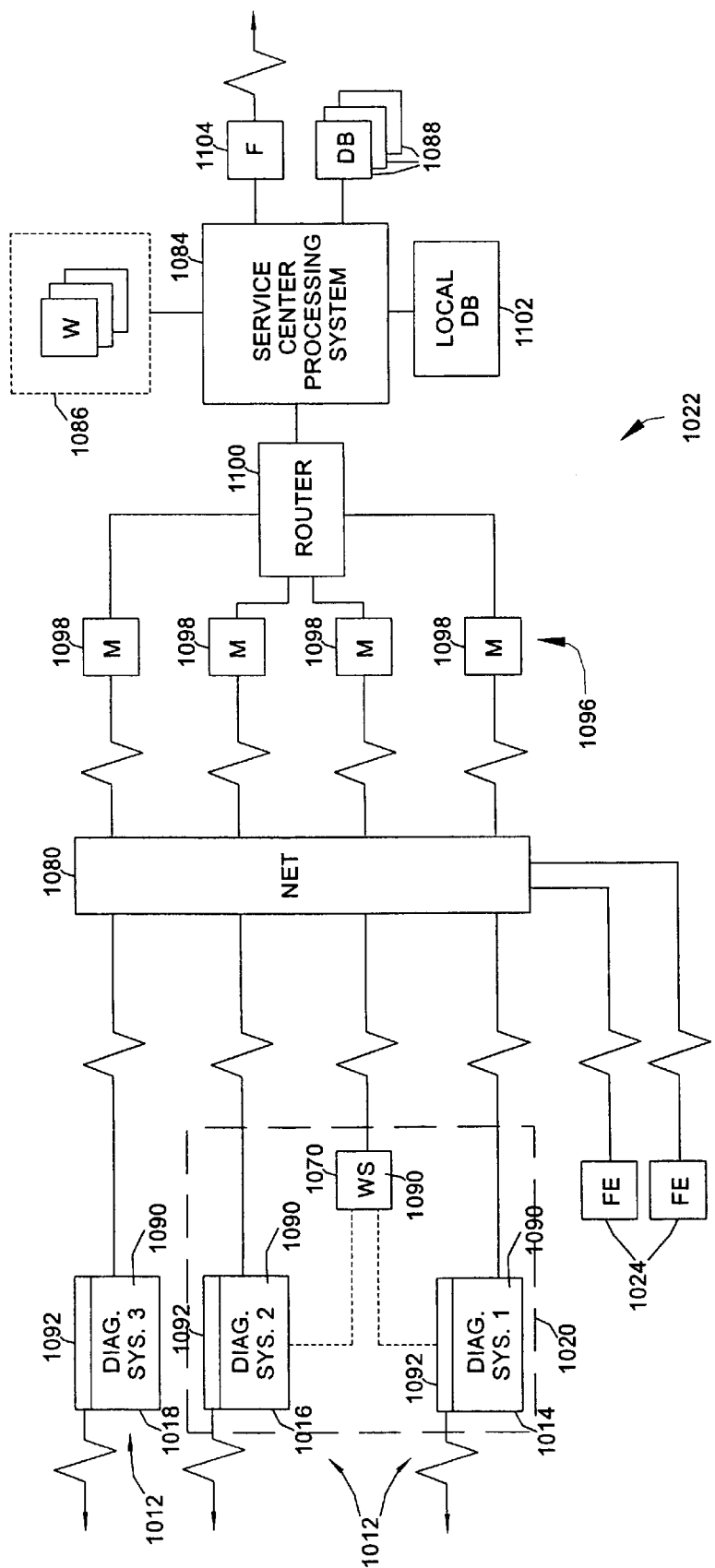
FIG. 3 is a block diagram of the systems shown in FIG. 2 illustrating certain functional components of the diagnostic systems and the service facility.

FIG. 3 is a block diagram illustrating the foregoing system components in a functional view. As shown in FIG. 3, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 4, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 3, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 4:
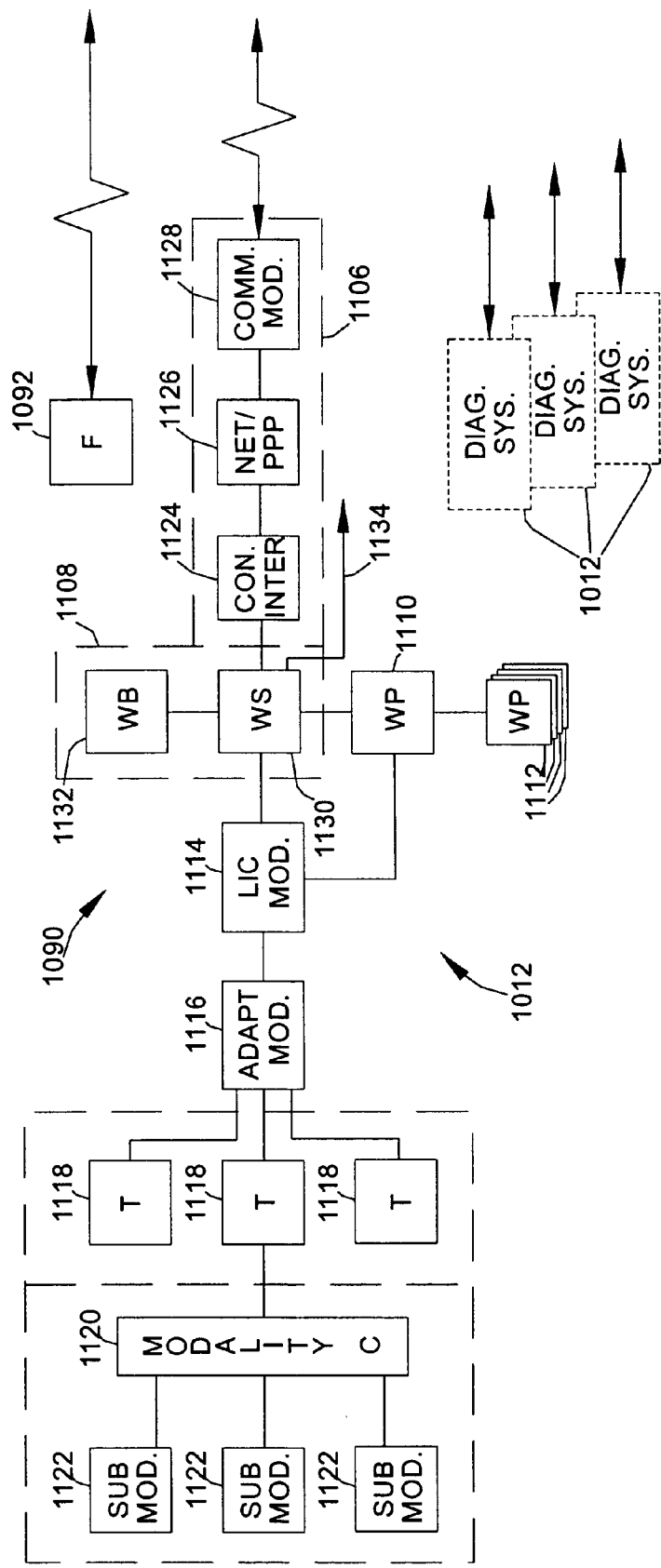
FIG. 4 is a block diagram of certain functional components within a diagnostic system of the type shown in FIG. 2 and FIG. 3 for facilitating interactive remote servicing of the diagnostic system.

FIG. 4 illustrates diagrammatically the various functional components comprising the uniform service platform 1090 within each diagnostic system 1012. As shown in FIG. 4, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 2 and 3).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 5:
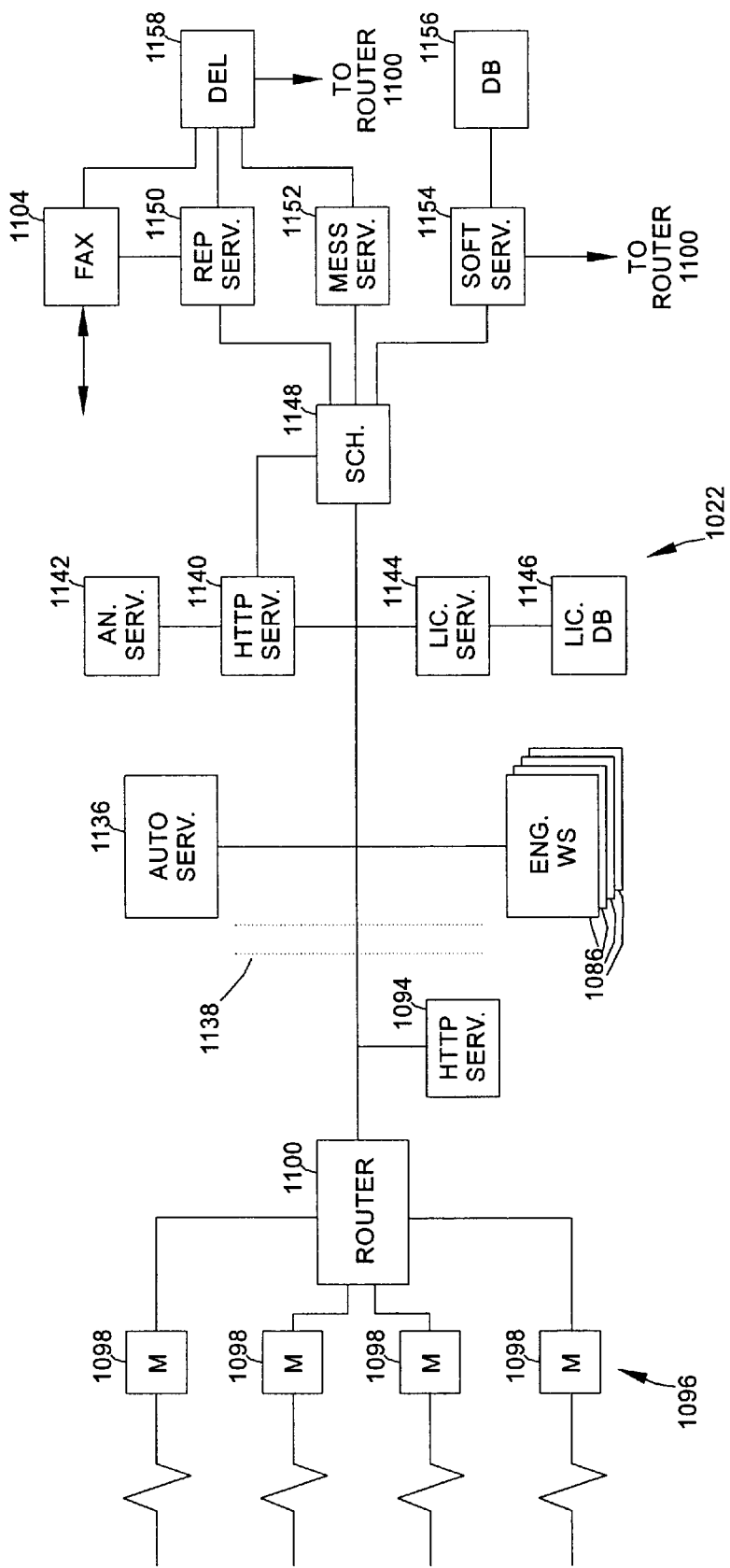
FIG. 5 is a block diagram of certain of the functional components of the service facility illustrated in FIG. 2 and FIG. 3 for rendering interactive remote service to a plurality of medical diagnostic systems.

FIG. 5 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 5, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 2) provides remote services, such as, remote upgrades, remote diagnostics, remote servicing, remote viewing, remote file storage, remote control, and remote adjustments to system parameters and functions. Furthermore, remote services may provide for contractual arrangements, such as, per use licenses which lease the medical diagnostic equipment based on use. Additionally, remote services may also include expert on-line assistance for image scanning techniques, image analysis, pathology detection, imaging unit maintenance, and other expert-aided operations.

While the embodiments illustrated in the Figures and described above are presently preferred, it should be understood that the embodiments are offered by way of example only. Other embodiments may include enhanced remote features made possible by the structures and functionalities described herein. The invention is not limited to a particular embodiment, but extends to various modifications, combinations, and permutations that nevertheless fall within the scope and spirit of the appended claims.

What is claimed is:

1. A method for converting a digital image to an analog-simulative film-like digital image comprising:

a. obtaining digital image input values for a number of pixels, each pixel having a digital image input value X, wherein the range of input values for all pixels defines the input dynamic range;

b. for each pixel, determining an analog-simulative film-like output value $$Y = \sum_{i=1}^{M} A_i X^{Pi} + B_i$$

wherein $A_i$, pi, and $B_i$ are real numbers, and

M is an integer value greater than or equal to 1; and c. communicating the analog-simulative film-like digital image or data associated therewith to a remote facility over a network.

2. The method of claim 1 wherein the step of determining an analog-simulative film-like output value Y includes:

a. for pixels having input values $X<X_1$ wherein $X_1$ is a value within the input dynamic range, determining for each pixel an analog-simulative film-like output value $$Y = \sum_{i=1}^{M} A_{l_i} X^{Pl_i} + B_{l_i}$$

wherein $A_{1i}$, $p_{1i}$, and $B_{1i}$ are real numbers,

M is an integer number greater than or equal to 1, and $p_{1i}>1$, b. for pixels having input values $X>X_2$ wherein $X_2$ is a value within the input dynamic range and $X_2 \geq X_1$, determining for each pixel an analog-simulative film-like output value $$Y = \sum_{i=1}^{M} A_{3i} X^{P3i} + B_{3i}$$

wherein $A_{3i}$, $p_{3i}$, and $B_{3i}$ are real numbers,

M is an integer number greater than or equal to 1, and $p_{3i}<1$.

3. The method of claim 2 wherein $A_{1i}<1$.

4. The method of claim 2 wherein $A_{3i}>1$.

5. The method of claim 2 wherein $X_2>X_1$, and further comprising the step, for pixels having input values $X_1 \leq X \leq X_2$, of determining for each pixel an analog-simulative film-like output value $$Y = \sum_{i=1}^{M} A_{2i} X^{P2i} + B_{2i}$$

wherein $A_{2i}$, $p_{2i}$, and $B_{2i}$ are real numbers,

M is an integer number greater than or equal to 1, and $p_{2i} \approx 1$.

6. The method of claim 5 wherein $A_{2i}>1$.

7. The method of claim 6 wherein $A_{1i}<1$.

8. The method of claim 6 wherein $A_{3i}>1$.

9. A method for converting a digital image to an analog-simulative film-like digital image comprising:

a. obtaining digital image input values from a number of pixels, each pixel having an input value X, wherein the range of input values for all pixels defines the input dynamic range;

b. for pixels having input values $X<X_1$ wherein $X_1$ is a value within the input dynamic range, determining for each pixel an analog-simulative film-like output value $Y=A_1 X^{p1}+B_1$ wherein $A_1$, $p_1$, and $B_1$ are real numbers and $p1>1$;

c. for pixels having input values $X>X_2$ wherein $X_2$ is a value within the input dynamic range and $X_2 \geq X_1$, determining for each pixel an analog-simulative film-like output value $Y=A_3 X^{p3}+B_3$ wherein $A_3$, $p_3$, and $B_3$ are real numbers and $p3<1$;

d. generating an output image in accordance with the output values of the pixels; and e. communicating the output image or image data to a remote facility over a network.

10. The method of claim 9 wherein $A_1<1$ and $A_3>1$.

11. The method of claim 9 further comprising the step of printing the output image on translucent film.

12. The method of claim 9 wherein $X_2>X_1$, and further comprising the step, for pixels having input values $X_1 \leq X \leq X_2$, of determining for each pixel an analog-simulative film-like output value $Y=A_2 X^{p2}+B_2$ wherein $A_2$, $p2$, and $B_2$ are real numbers and $p2 \approx 1$.

13. The method of claim 12 wherein $A_2>1$.

14. The method of claim 13 wherein $A_1<1$ and $A_3>1$.

15. A method for converting a digital image to an analog-simulative film-like digital image comprising:

a. obtaining digital image input values from a number of pixels, each pixel having an input value X ranging between $X_{min}$ and $X_{max}$, the range between $X_{min}$ and $X_{max}$ defining the dynamic range of the input values;

b. dividing the dynamic range into N intervals, N being an integer number of at least 1;

c. for each interval, determining for each input value therein an analog-simulative film-like output value $$Y = \sum_{i=1}^{M} A_i X^{P_i} + B_i$$

wherein

M is an integer value greater than or equal to 1,

X is the input value, $A_i$, $p_i$, and $B_i$ are real numbers, and $p_i$ decreases with each interval after a first interval adjacent Xmin; and d. generating an output image in accordance with the output values of the pixels; and e. communicating the output image or image data to a remote facility over a network.

16. The method of claim 15 wherein the $B_i$ term(s) are chosen to provide a continuous curve for Y as X varies across the N intervals.

17. The method of claim 15 further comprising the step of printing the output image on translucent film.

18. The method of claim 15 wherein:

a. $p_i>1$ for at least one interval close to $X_{min}$, and b. $p_i<1$ for at least one interval close to $X_{max}$.

19. The method of claim 18 wherein $N \geq 3$, and wherein $p_i \approx 1$ for at least one interval between $X_{min}$ and $X_{max}$.

20. The method of claim 15 wherein $N \geq 3$, and wherein $A_i>1$ for at least one interval between a first interval adjacent $X_{min}$ and a last interval adjacent $X_{max}$.

* * * * *